(12) United States Patent
Bartsch et al.

(10) Patent No.: US 6,177,616 B1
(45) Date of Patent: *Jan. 23, 2001

(54) GENES CODING FOR AMINO ACID DEACETYLASES WITH SPECIFICITY FOR N-ACETYL-L-PHOSPHINOTHRICIN, THEIR ISOLATION AND THEIR USE

(75) Inventors: Klaus Bartsch, Königstein; Guido Kriete, Halle; Inge Broer, Roggentin; Alfred Pühler, Bielefeld, all of (DE)

(73) Assignee: Hoecsht Schering Agrevo GmbH, Berlin (DE)

( * ) Notice: Under 35 U.S.C. 154(b), the term of this patent shall be extended for 0 days.

This patent is subject to a terminal disclaimer.

(21) Appl. No.: 09/319,892

(22) PCT Filed: Dec. 3, 1997

(86) PCT No.: PCT/EP97/06755

§ 371 Date: Jun. 14, 1999

§ 102(e) Date: Jun. 14, 1999

(87) PCT Pub. No.: WO98/27201

PCT Pub. Date: Jun. 25, 1998

(30) Foreign Application Priority Data

Dec. 16, 1996 (DE) .............................. 196 52 284

(51) Int. Cl.⁷ .......................... C12N 15/05; C12N 15/31; C12N 15/63; C12N 15/82; A01H 5/00

(52) U.S. Cl. .......................... 800/303; 800/278; 800/295; 800/287; 800/298; 800/288; 435/69.1; 435/252.2; 435/468; 435/419; 536/23.1; 536/23.2; 536/23.7; 536/24.1

(58) Field of Search ..................................... 800/278, 295, 800/298, 303, 287, 288; 435/69.1, 252.2, 468, 419; 536/23.1, 23.2, 23.7, 24.1

(56) References Cited

U.S. PATENT DOCUMENTS 5,650,310 * 7/1997 Broer et al. ...................... 435/172.3

FOREIGN PATENT DOCUMENTS

| 2 258 448 | 8/1975 | (DE) . |
| 41 26 414A | 2/1993 | (DE) . |
| 0531716 | 3/1993 | (DE) . |
| 43 08 061 | 9/1994 | (DE) . |
| 196 39 463 | 4/1998 | (DE) . |

OTHER PUBLICATIONS

Kriete et al. The Plant Journal, vol. 9, No. 6, pp. 809–818, Feb. 1996.*

Turgut et al. Plant Molecular Biology, vol. 24, pp. 97–104, 1994.*

Thorness et al. Developmental Biology, vol. 143, 173–184, 1991.*

Goldman et al. The EMBO Journal, vol. 13, No. 13, pp. 2976–2984, 1994.*

Kanadasamy et al. The Plant Cell, vol. 5, pp. 263–275, Mar. 1993.*

Leyh et al. The Journal of Biological Chemistry, vol. 267, No. 15, pp. 10405–10410, May 1992.*

Kriete et al., "Male Sterility in Transgeneic Tobacco Induced by Tapetum–Specific Deacetylation of the Externally Applied Non–toxic Compound n–acetyl–l–phophinothricin", Plant Journal, vol. 9, No. 6, 1996, pp. 809–828.

* cited by examiner

Primary Examiner—David T. Fox
Assistant Examiner—Medina A. Ibrahim
(74) Attorney, Agent, or Firm—Frommer Lawrence & Haug LLP (57) ABSTRACT

The invention relates to DNA molecules which code for deacetylases or proteins having the biological activity of a deacetylase and also transgenic plant cells which were transformed using the DNA molecules according to the invention. These molecules can be used for the production of plants having specifically destroyable parts, i.e. male- or female-sterile plants, by means of the specific expression of a deacetylase gene.

13 Claims, 5 Drawing Sheets

GENES CODING FOR AMINO ACID DEACETYLASES WITH SPECIFICITY FOR N-ACETYL-L-PHOSPHINOTHRICIN, THEIR ISOLATION AND THEIR USE

CROSS-REFERENCE TO RELATED APPLICATIONS

This application corresponds to PCT/EP97/06755 filed Dec. 3, 1997, designating the U.S. which claims priority from German Patent Application 196 52 284.6 filed Dec. 16, 1996. Each of these documents are incorporated herein by reference.

BACKGROUND OF THE INVENTION

The concept of a chemically inducible, reversible male sterility in plants by anther-specific expression of an N-acetylphosphinothricin (N-acetyl-PPT)-specific deacetylase is described in European Patent Application EP 531 716. The deacetylase genes from Streptomyces viridochromogenes [N-acetyl-L-phosphinothricylalanylalanine (N-acetyl-PTT) deacetylase, dea] and argE from *Escherichia coli* (N-acetyl-L-ornithine deacetylase) used here encode proteins having specificity for N-acetyl-L-PPT. For both genes, it was possible in the case of tapetum-specific expression in plants to show the occurrence of male-sterile flowers after treatment of individual buds with N-acetyl-L-PPT. For successful use of this system, in particular in the treatment of whole plants with N-acetyl-PPT under practically relevant conditions, it is advantageous to be able to employ deacetylases having high substrate affinity. Therefore further deacetylases having high affinity for N-acetyl-PPT were sought.

OBJECTS OF THE INVENTION

The application described here is thus based on the object of making available DNA molecules which code for deacetylases. Using these deacetylases, it is possible to produce plants having plant parts which can be destroyed specifically. The production of male- or female-sterile plants is of particular interest. The object is achieved by the provision of the embodiments described in the patent claims.

SUMMARY OF THE INVENTION

The invention relates to DNA molecules which code for deacetylases or proteins with the biological activity of a deacetylase. The enzymatic properties of these proteins are described in the examples. The invention also relates to DNA molecules which encode a biologically active subfragment or a derivative. The molecules according to the invention also include fragments, derivatives or allelic variants. Fragments are understood as meaning parts which still have the biological activity of a deacetylase.

The invention additionally relates to transgenic plant cells which have been transformed using the DNA molecules according to the invention. The transgenic plant cells can be prepared according to known techniques and are regenerated to give whole plants.

The invention relates to DNA molecules encoding a protein having the biological activity of an N-acetyl-PPT deacetylase.

The invention relates in particular to DNA molecules encoding a protein having the biological activity of an N-acetyl-PPT deacetylase selected from the group consisting of a) DNA molecules which code for a protein having the amino acid sequence indicated under SEQ ID No 2 and fragments and/or derivatives thereof;

b) DNA molecules which code for a nucleotide sequence indicated under SEQ ID No 1 or sequences which deviate from this sequence within the bounds of code degeneracy;

c) DNA molecules which code for a protein having the amino acid sequence indicated under SEQ ID No 4 or fragments and/or derivatives thereof and d) DNA molecules which code for a nucleotide sequence indicated under SEQ ID No 3 or sequences which deviate from this sequence within the bounds of code degeneracy.

The invention additionally relates to the microorganisms Stenotro-phomonas sp. (DSM 9734) and Comamonas acidovorans (DSM 11070) identified and deposited according to the method described in this application.

The invention relates in particular to plant cells or plants which contain the DNA molecules according to the invention.

Of particular interest are processes for the production of plants with specifically destroyable parts by means of specific expression of a deacetylase gene and processes for the production of male- or female-sterile plants by means of specific expression of a deacetylase gene.

The present application thus also relates to:

(1) the specific concentration of microorganisms having high N-acetyl-PPT deacetylase activity (2) the isolation of corresponding deacetylase genes (3) the purification and characterization of the proteins having high N-acetyl-PPT deacetylase activity encoded by these genes (4) the expression of the deacetylase genes in plants.

The present application additionally relates to:

the DNA molecules which code for enzymes having high N-acetyl-PPT deacetylase activity the proteins which are encoded by these genes the expression of these deacetylase genes in plants.

From soil samples, bacteria can be concentrated in mineral medium with chitin as the sole carbon source which are able to cleave N-acetyl-PPT with high effectiveness. In this manner, 2 bacterial strains were isolated as pure cultures: Stenotrophomonas sp. (DSM deposit No. DSM 9734) and Comamonas acidovorans (DSM deposit No. 11070).

For the conditions necessary in industrial production, however, it is substantially more advantageous to be able to employ a purified enzyme.

The present application comprises novel L-N-acetyl-PPT specific deacetylases, a novel and effective process for the purification and characterization of this enzyme from a concentration culture of soil microorganisms, and the use of this deacetylase.

The invention thus further relates to:

1. A deacetylase having
   a molecular weight of 20,000 to 100,000 Daltons
   a pH optimum of 6.5–10.0
   a substrate specificity to L-N-acetyl-phosphinothricin.
2. A process for the preparation of a deacetylase, which comprises culturing a microorganism which does not form spores in a medium comprising crab chitin, and isolating the deacetylase from these microorganisms.
3. The use of the deacetylase characterized under 1. for the production of male-sterile plants and for the stereoselective preparation of L-phosphinothricin.

The invention relates in particular to an enzyme which has a temperature optimum which lies between 30° C. and 50° C.

DETAILED DESCRIPTION OF THE INVENTION

The process according to the invention for the preparation of the deacetylases is preferably carried out using microorganisms selected from the group which consists of the microorganisms described in the application.

Crab chitin can be obtained as described by Shimahara, Kenzo and Takiguchi, Yasuyuki (Methods in Enzymology, Vol 161, pages 417–423, 1988) or is commercially available from Sigma.

To purify the deacetylase, the microorganism is cultured in a nutrient medium optimal for its growth. The microorganism is cultured aerobically, for example submerse with shaking or stirring in shaker flasks or fermenters, if appropriate with introduction of air or oxygen. The fermentation can be carried out in a temperature range from approximately 20 to 40° C., preferably at approximately 25 to 37° C., in particular at 30 to 37° C. Culture takes place in a pH range between 5 and 8.5, preferably between 5.5 and 8.0.

Under these conditions, the microorganisms in general show a noticeable accumulation of the enzyme after 1 to 3 days. The synthesis of the deacetylase begins with the log phase. The production of the enzyme can be monitored with the aid of activity tests by HPLC analysis or photometrically. The nutrient solution used for the production of the transaminase contains 0.2 to 5%, preferably 0.5 to 2%, of crab chitin and inorganic salts.

Inorganic salts which the nutrient medium can contain are, for example, chlorides, carbonates, sulfates or phosphates of the alkali metal or alkaline earth metals, iron, zinc and manganese, but also ammonium salts and nitrates.

According to the invention, effective amounts of the deacetylase can be employed in free or immobilized form for the deacetylation, preferably it is employed in plants which express dea genes.

For fixation, the known processes are suitable, such as the processes described in German Offenlegungsschriften 32 37 341 and 32 43 591.

The enzyme can be isolated and purified by classical methods by means of decomposition by ultrasound and French press, ammonium sulfate precipitation, ion exchangers, affinity chromatography and gel permeation.

The enzyme preparation can have a molecular weight of 20,000 to 100,000 Daltons, preferably 30,000 to 80,000, in particular 40,000 to 70,000 Daltons. The pH optimum of the enzyme product lies in the pH range 6.0 to 10.0, in particular 7.0 to 8.0. The temperature optimum of the enzyme lies between 30 and 50° C., in particular between 35 and 45° C. The genes coding for the deacetylases were cloned in *E. coli*. In the case of the deac1 gene from Stenotrophomonas sp., a phagemid expression bank from genomic DNA in *E. coli* was screened for N-acetyl-PPT-specific deacetylase activity. The deac2 gene from Comamonas acidovorans was cloned with a genomic bank by complementation of an *E. coli* - argE mutant.

The amino acid sequences derived from the DNA sequences of the two genes are similar to one another and additionally have homology to hippurate hydrolases, as are known from protein databanks.

The high substrate affinity of the deacd protein for N-acetyl-L-PPT ($K_m$=670 $\mu$M) makes itself noticeable in the transgenic plants by a high sensitivity of the tissue to this substance. Thus in constitutive expression of the deac gene plants can be obtained whose leaves still react sensitively to concentrations of up to 0.4 mg/ml of N-acetyl-D,L-PPT (=0.2 mg/ml of L-enantiomer). In the case of tapetum-specific expression, the induction of male-sterile flowers was achieved by treatment of the buds with 2 mg/ml of N-acetyl-D,L-PPT (=1 mg/ml of L-enantiomer). The results described relate to greenhouse plants. On the basis of the low substance concentrations, if required, under open air conditions a higher dose of around 5–10-fold is possible without problems.

EXAMPLES

The following examples serve to illustrate the invention more extensively. Percentage data, if not stated otherwise, relate to the weight. The invention is defined further in the patent claims.

Example 1

Isolation and Identification of Soil Microorganisms having an N-acetyl-PPT-specific Deacetylase Activity Each 1 g of soil (sandy loam, Schwanheimer dune) was extracted for 1 h at room temperature with 10 mM NaCl, 10 mM Na phosphate buffer, pH=7.0. To select various groups of microorganisms, the soil supernatants were transferred to the following liquid media:

(1) MS1 medium (for Eubacteria):
  5 mM glucose
  5 mM succinate
  10 mM glycerol
  1 g/l of NH$_4$Cl
  50 ml/l of solution A
  25 ml/l of solution B
    Solution A: 50 g/l of K$_2$HPO$_4$
    Solution B: 2.5 g/l of MgSO$_4$
    0.5 g/l of NaCl
    25 ml/l of trace elements (2) Chitin medium (for Actino- and Streptomycetes, and chitinovorous bacteria):
  10 g/l of crab chitin
  1 g/l of (NH$_4$)$_2$SO$_4$
  0.5 g/l of MgSO$_4$
  50 ml/l of solution A
  1 ml/l of trace elements (3) Antibiotic medium (for higher fungi):
  20 g/l of malt extract
  10 g/l of glucose
  2 g/l of yeast extract
  0.5 g/l of (NH$_4$)$_2$SO$_4$
  50 $\mu$g/ml of tetracycline All media contained 5 mM N-acetyl-PPT and were incubated for 3–5 days at 28° C. after transferring.

The concentration cultures were then tested for deacetylation of N-acetyl-PPT. To do this, the cells were centrifuged off at 10,000 rpm and the supernatants were investigated for formation of PPT in an amino acid analyzer (Biotronic LC 5001). Only the chitin medium cultures proved to be deactylase-positive. After plating out on chitin-agar, a total of 40 individual colonies were isolated from these cultures, recultured in chitin liquid medium and tested again for deacetlyase activity. Six positive isolates were found here, from which it was possible to obtain the active pure cultures by repeated streaking out on agar plates and further culturing of individual colonies. The strain with the highest deacetylase activity was identified as Stenotrophomonas sp. (DSM deposit No. DSM 9734).

Example 2

Cloning and Sequencing of the N-acetyl-PPT Deactylase Gene from Stenotrophomonas sp.

The standard molecular biology methods used for the studies are described in Maniatis et al. 1982, Molecular Cloning: a laboratory manual, Cold Spring Harbor Laboratory, Cold Spring Harbor, N.Y.

Figure 1:
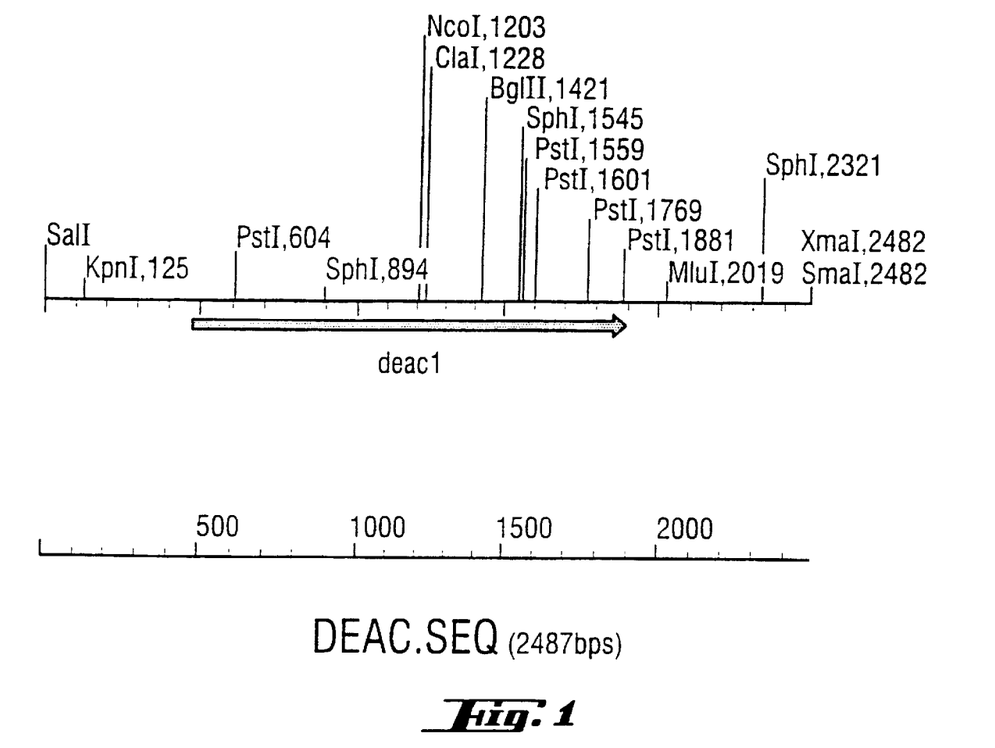
FIG. 1 Restriction map of the 2.5 kb SalI/BamHI fragment which mediates the N-acetyl-PPT-specific deacetylase activity. Position and orientation of the deac1 structural gene are marked by an arrow (BP=base pairs).

Genomic DNA from Stenotrophomonas sp. was prepared according to the method of Meade et al., 1982, J. Bacteriol. 149:114–122. After partial digestion with Sau3A, the 5–10 kb size fraction was isolated and ligated in the lambda-ZAP express vector, which was cleaved with BamHl, from Stratagene (ZAP Express Vector Kit, Catalog No. 239201, Instruction Manual). Using the packaged ligation batch, a primary lambda-phage bank was prepared and then amplified. A phagemid expression bank in *Escherichia coli* was prepared from this with the aid of the pBK-CMV phagemid system from Stratagene (Catalog No. 212209, Instruction Manual). This gene bank was tested for the presence of the deactylase gene by activity screening with [$^{14}$C]-N-acetyl-L-PPT as a substrate. For this purpose, 2000 individual clones were transferred to microtiter plates and cultured overnight in LB medium at 37° C. with 0.2 mM isopropyl thiogalactoside (IPTG) as an inducer and 50 μg/ml of kanamycin as a resistance marker. The cells were centrifuged off and incubated overnight at 28° C. in 10 μl each of 1 mM [$^{14}$C]-N-acetyl-L-PPT. The batches were then analyzed in pools of eight for conversion of N-acetyl-PPT into PPT by thin-layer chromatography and autoradiography (see EP 531 716, Example 8) and the individual clones retested in the case of a positive result. Using this method, it was possible to select from 1920 transformants a positive clone having a 6 kb insert. This DNA fragment was characterized in greater detail by restriction mapping. By subcloning restriction fragments of the inserts in pUC18/19 and transformation of the recombinant plasmids in *E. coli*, it was possible with the aid of the activity test described above to localize the deac structural gene on a 2.5 kb (2487 base pairs) SalI/SmaI fragment (FIG. 1). The activity was dependent on the orientation of the fragment relative to the lac promoter of the vector.

The 2.5 kb fragment was sequenced on both strands using the Sanger method (Sanger et al. 1977, Proc. Natl. Acad. Sci USA 74:5463–5468). The entire fragment has a length of 2487 nucleotides (see SEQ ID NO. 1). The open reading frame of 1494 nucleotides length begins with nucleotide No. 367 and ends with No.1860.

Expression studies with PCR subfragments from this region in *E. coli* showed that the active deactylase protein is encoded by a region 1365 nucleotides long beginning with the ATG start codon in position 496 and ending with the TGA stop codon in position 1860. The amino acid sequence derived from the DNA sequence is a polypeptide of 454 amino acids (Seq ID NO 2) having a calculated molecular weight of 48.1 kDa.

A homology search in the EMBL, DNA and protein databanks showed similarities to the N-acetyl-PPT deactylase from Comamonas acidovorans described in this application for the first time (37.4% identical amino acids), the hippurate hydrolase from Campylobacter jejuni (33.9%) and N-acyl-L-amidohydrolase from Bacillus stearothermophilus (33.7%). Below, the gene isolated from Stenotrophomonas is described as deacd. The corresponding protein is described as Deac1. On account of the homology, it can be assumed that the hippurate hydroiases and amidohydrolases mentioned can also advantageously be used in combination with tissue-specific promoters and a subsequent treatment for the preparation of plants having selectively destroyable tissues, in particular male and/or female-sterile plants.

Example 3

Characterization of the Deac1 Protein

To overexpress and purify the deactylase from Stenotrophamonas sp. (deac1), the glutathione S-transferase (GST) gene fusion vector system from Pharmacia (Catalog No. 27-4581-01, Catalog No. 27-4570-01) was used. The method is described in Smith and Johnson, 1988, Gene 67:31. The fusion proteins are purified by affinity chromatography on glutathione-Sepharose 4B.

The functional deac gene was recloned into the GST fusion vector pGEX-4T-2 under control of the lac promoter as a 1.4 kb BamHI/SalI PCR fragment. The expression of recombinant fusion protein was induced by addition of 0.1 mM IPTG. By SDS/polyacrylamide electrophoresis of crude extracts of the *E. coli* transformants, it was possible to detect the fusion protein as a 74 kDa band.

To purify the protein, the cells of a 2 l culture of an induced, expression-positive *E. coli* transformant were disrupted with ultrasound and the extract was then solubilized by addition of 1% Triton X-100. The supernatant was bound to glutathione-Sepharose 4B. After repeated washing with PBS buffer (140 mM NaCl, 3 mM KCL, 10 mM Na$_2$HPO$_4$, 2 mM KH$_2$PO$_4$, pH=7.3), the fusion protein bound to the Sepharose matrix was cleaved with thrombin. The eluate contained as the only protein band a cleavage product of 48 kDa (after denaturing SDS/polyacrylamide electrophoresis), which was identified in the enzyme assay (see below) as N-acetyl-PPT deactylase. Using the method described, it was possible to purify 200 μg of deactylase protein to homogeneity from 2 l of bacterial culture.

The activity of the deacetylase protein was measured using the two following assays:

(1) Radioactive test: 2.5 μg each of purified enzyme was incubated with 0.1 mM [$^{14}$C]-N-acetyl-L-PPT for 15 min. at 37° C. in 10 μl batches in PBS buffer. The samples were then diluted 1:6 in 5 mM KH$_2$PO$_4$, 10% methanol, pH=1.92 and analyzed in the HPLC using a radioactivity detector (separating column: Spherisorb SAX, eluent: 5 mM KH$_2$PO$_4$, 10% methanol, pH=1.92, flow rate: 0.5 ml/min). Under these conditions, [$^{14}$C]-L-PPT elutes at 4.5 min. and[$^{14}$C]-N-acetyl-L-PPT elutes at 6.5 min. The specific deacetylase activities were determined in [nmol of [$^{14}$C]-L-PPT/min/mg of protein]. To determine the pH optimum, the batches were incubated between pH=6 and 9 in a buffer system of, in each case, 40 mM bis-tris, tris and caps. For the K$_m$ value measurement, 3-fold determinations were carried out at pH=8.0 in the presence of 1 mM CoCl$_2$ using concentrations of [$^{14}$C]-N-acetyl-L-PPT of between 0.01 mM and 1 mM.

(2) Nonradioactive test: To investigate the substrate specificity, 5 μg each of purified enzyme were incubated for 60 min. at 28° C. in 20 μl batches in PBS buffer with, in each case, 25 mM of a certain N-acetyl- or N-acylamino acid. The samples were then measured in an amino acid analyzer (Biotronic LC 5001) for formation of the free amino acids. The specific activities were determined in [nmol of amino acid/min/mg of protein]. For the N-acetyl-PPT deacetylase, a pH optimum of pH=8 (see Tab. 1) and a temperature optimum of 37° C. (see Tab. 2) were determined. The kinetic measurements showed a $K_m$ value of 670 μM. By addition of 1 mM $CoCl_2$, the enzyme activity could be increased by about 20%.

TABLE 1 pH optimum of the N-acetyl-PPT deacetylase

| pH | Spec. activity [mol/min/mg of protein] |
|---|---|
| 6 | 2.4 |
| 7 | 7.2 |
| 8 | 12.0 |
| 9 | 8.5 |

TABLE 2

Temperature optimum of the N-acetyl-PPT deacetylase

| Temperature [° C.] | Spec. activity [nmol/min/mg of protein]: |
|---|---|
| 28 | 9.6 |
| 37 | 16.8 |
| 50 | 14.9 |
| 60 | 4.3 |

The results of the measurements of substrate specificity are shown in Tab. 3.

The enzyme has a relatively wide substrate spectrum. The highest conversions were achieved with hippuric acid (N-benzoylglycine) and N-acetyl-L-glutamate. The affinity for N-acetyl-L-PPT lies approximately 50% below that for the two abovementioned substrates. The deacetylase has an exclusive specificity for N-acetyl-L-amino acids. Using the corresponding D enantiomers, no reactions were observed.

TABLE 3

Substrate specificity of the N-acetyl-PPT deacetylase

| Substrate[1] | Rel. activity[2] [%] |
|---|---|
| Hippuric acid (N-benoylglycine) | 100 |
| N—Ac-phosphinothricin | 43 |
| N—Ac-ornithine | 37 |
| N—Ac-methionine | 0 |
| N—Ac-tryptophan | 0.4 |
| N—Ac-phenylalanine | 24 |
| N—Ac-tyrosine | 11 |
| N—Ac-glutamic acid | 100 |
| N—Ac-glutamine | 30 |
| N—Ac-glycine | 59 |
| N—Ac-histidine | 43 |
| N—Ac-leucine | 33 |
| N—Ac-valine | 2 |
| N—Ac-serine | 4 |
| N—Ac-proline | 0 |

[1]In all compounds these are the L-enantiomers.
[2]The specific activity measured with hippuric acid was set equal to 100% and the other values were related to it.

Example 4

Constitutive Expression of the Deac1 Gene in Tobacco

Figure 2:
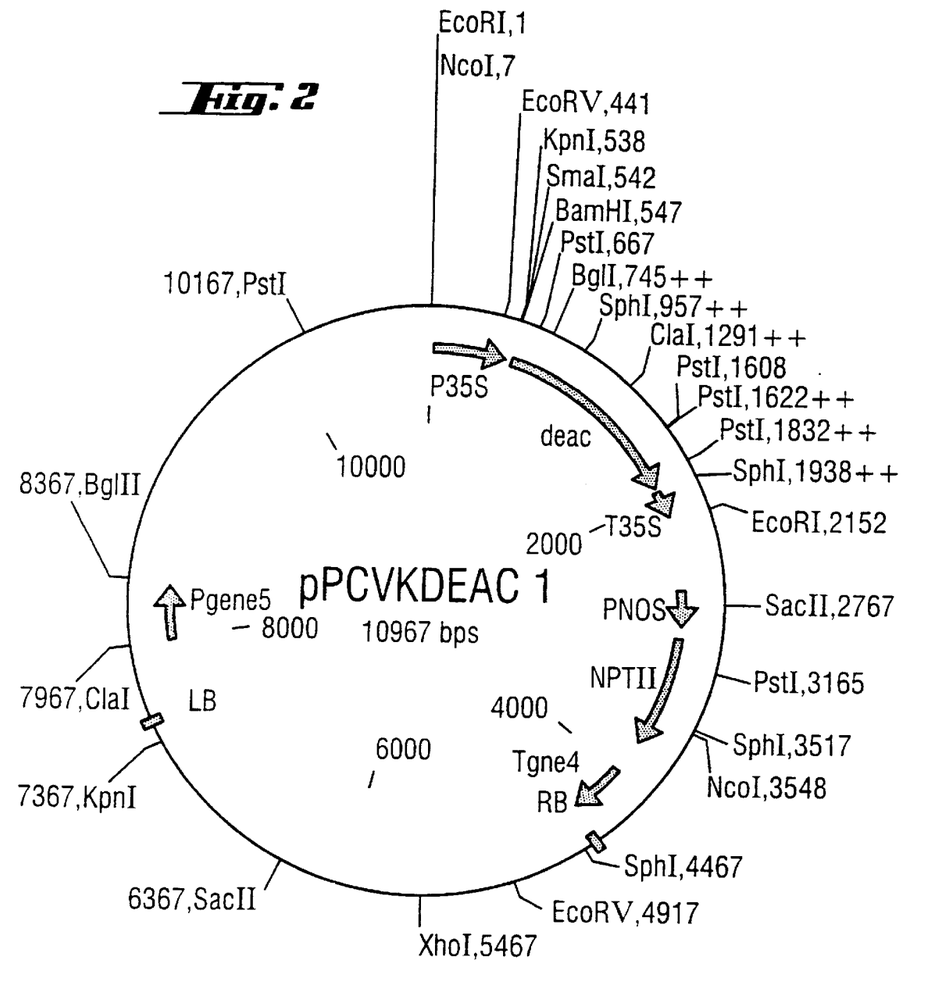
FIG. 2 Map of the plasmid pPVCKDEAC1 for the constitutive expression of the deac gene in plants FIG. 3 Map of the plasmid pPCVTDEAC1 for the tapetum-specific expression of the deac gene in plants FIG. 4 Map of the plasmid pGK83

The deac1 structural gene was recloned as a 1.4 kb BamHI/SalI PCT fragment into the binary vector pPCV801 (Koncz and Schell, 1986, Mol. Gen. Genet. 204: 383–396) under control of the 35S promoter. The resulting plasmid pPCVKDEAC1 (FIG. 2) with the expression vector 35S promoter-deac1-structural gene-35S terminator was transformed in Agrobacterium tumefaciens (strain ATHV) using standard methods. Pieces of tobacco leaf (Nicotiana tabacum) were transformed with the recombinant Agrobacteria according to the method of Horsch et al., 1985, Science 227: 1229–1231 and selected on kanamycin medium, 18 independent tobacco transformants were regenerated and tested for expression of the deacetylase in the leaves. In the case of activity of the protein in the transgenic plants, a sensitivity of the leaves to N-acetyl-PPT was to be expected, because the substance in the plant is then converted into the herbicidal active compound phosphinothricin on account of the enzymatic activity of the deacetylase.

In a drop experiment, the leaves of the transgenic plants and of a number of nontransgenic control plants were treated with 5 μl each of the following concentrations of N-acetyl-D,L-PPT: 4 mg/ml (=15 mM), 1 mg/ml (=3.75 mM), 0.4 mg/ml (=1.5 mM), 0.1 mg/ml (=0.38 mM). The treatment sites were examined for lightening or necrosis formation after 1–2 weeks. Simultaneously, the N-acetyl-PPT-specific deacetylase activity of the transformants, and also of the control plants, was measured in crude extracts. To do this, 100 mg each of leaf material were homogenized in 200 μl of PBS buffer, the cell debris was centrifuged off and the protein-containing supernatants were dialyzed overnight at 4° C. against the same buffer. 10 μl each of these samples were incubated with 0.1 mM [$^{14}$C]-N-acetyl-L-PPT overnight at 37° C. The batches were then analyzed in the HPLC, as described above, for formation of [$^{14}$C]-L-PPT.

The test results of the drop experiments and the activity tests are shown in Tab. 4 for selected plants. It is seen that about 60% of the transformants express the functional deacetylase protein and show the corresponding phenotype.

TABLE 4

Sensitivity of pPCVKDEAC1 plants to N-acetyl-PPT and deacetylase activity in crude extracts

| | Drop experiment with: N—Ac-D,L-PPT | | | | Deac. activity in the crude extract |
|---|---|---|---|---|---|
| Plants | Observations (leaf;) | 4 mg/ml | 1 mg/ml | 0,4 mg/ml | 0,1 mg/ml | [% L-PPT][1] |
| Control | – | – | – | – | 0 |
| pPCVK9 | | +++ | + | – | – | 14.2 |
| pPCVK14 | curled | + | + | – | – | 12.1 |
| pPCVK15 | curled | ++ | + | + | – | 36.0 |
| pPCVK16 | curled | + | + | – | – | 4.7 |
| pPCVK17 | curled | + | + | – | – | 4.3 |

[1]based on the radioactivity employed ([$^{14}$C]—N-acetyl-L-PPT)
+++: severe necrosis
++: marked damage
+: slight lightening
–: no symptoms Example 5

Tapetum-specific Expression of the deac1 Gene in Tobacco

Figure 3:
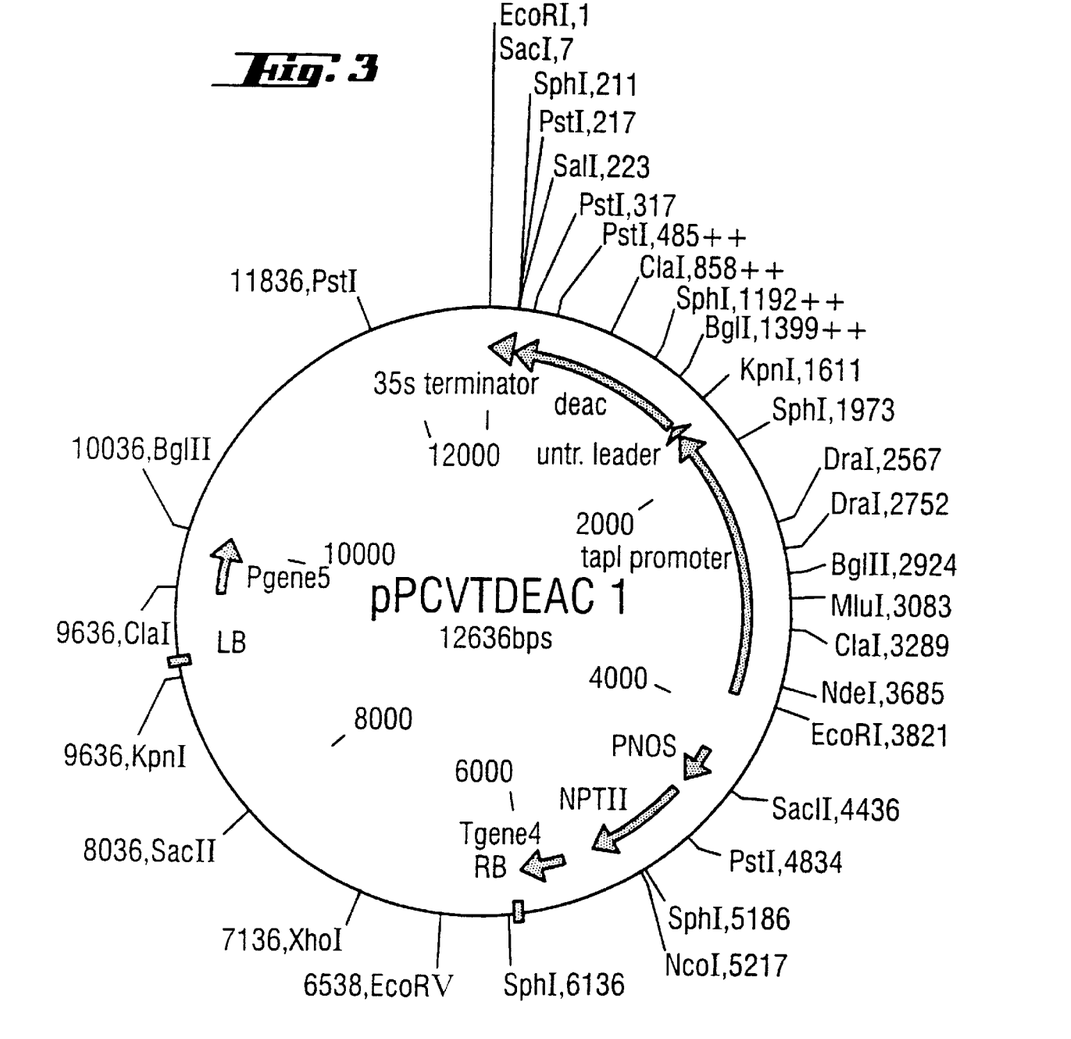

Using standard methods, the tapetum-specific promoter of the tap1 gene from snapdragon (Antirrhinum majus) was fused in the vector pUC18 as a 2.2 kb EcoRI/BamHI fragment with the deac1 structural gene (1.4 kb BamHI/SalI-PCR fragment) and the 35S terminator. The expression cassette tap 1 promoter-deac structural gene-35S terminator thus resulting was cloned into the binary vector pPCV801 as a 3.8 kb EcoRI fragment instead of the 35S promoter/terminator region (plasmid pPCVTDEAC1, FIG. 3). The transformation of tobacco was carried out as described in Example 4.

In the case of tapetum-specific expression of the deacetylase, it should be possible by treatment of the flower buds with N-acetyl-PPT to induce male-sterile flowers. The conversion of the PPT derivative into the herbicidal active compound phosphinothricin leads to selective damage to the tapetum tissue, by means of which the development of functional pollen is prevented.

In each case only one side of the inflorescences (the total area of the developing flower buds) was treated with N-acetyl-PPT, the other side of the influorescences remained untreated in order to ensure that the phenomena to be observed are not to be attributed to deformities of the respective plants. The treatment was carried out at a time at which the individual buds were not larger than 5 mm (active phase for tapetum promoter). The tobacco transformants and also a number of NT Sam NN control plants were treated 3× with 0.2% N-acetyl-D,L-PPT (=7.5 mM)/0.1 % Genapol (wetting agent) within one week. After the blooming of the buds (about 9–11 days after conclusion of the treatment), the plants were investigated for the occurrence of male-sterile flowers.

Simultaneously, the N-acetyl-PPT-specific deacetylase activity in immature anthers of the transformants, and also of the control plants, was measured. To do this, the immature anthers were dissected from flower buds about 5 mm in size and incubated overnight at room temperature in 50 $\mu$M [$^{14}$C]-N-acetyl-L-PPT solution in each case. The anthers were subsequently washed 1× in 500 $\mu$l of PBS buffer and then homogenized in 50 $\mu$l of PBS buffer. After centrifuging off the cell debris, the supernatants were concentrated in a Speed-Vac and the pellets were taken up in 30 $\mu$l each of HPLC buffer (5 mM $KH_2PO_4$, 10% methanol, pH=1.92). The batches were analyzed for formation of [$^{14}$C]-L-PPT in the HPLC, as described above.

The results of the flower treatment and of the activity test are shown for selected plants in Tab. 5. In almost all transformants, it was possible to determine an anther-specific deacetylase activity. In 3 transformants, male-sterile flowers, i.e. no pollen was formed, or severely pollen-reduced flowers were observed on the side of the flower cluster treated with N-acetyl-PPT. The effects on new, maturing buds lasted for a period of about 3 weeks. The untreated flowers of the transformants, and also the treated flowers of the control plants, were fertile in all cases. With the male-sterile flowers, no seed formation was determinable. A specific cross pollination of the male-sterile flowers was possible, however, by means of which it was proven that the female flower parts have kept their full functionality (Nacken et al, 1991, Mol.Gen. Genet. 229: 129–136).

TABLE 5

Induced male sterility in pPCVTDEAC1 plants by flower treatment with N-acetyl-PPT and deacetylase activity in anthers

| Plant | Number of sterile or pollen-reduced flowers | | Deac. activity in anthers |
| --- | --- | --- | --- |
| | treated | untreated | [% L-PPT][1] |
| Control | 0 | 0 | 0 |
| pPCVT14 | 18 | 0 | 70.0 |
| pPCVT15 | 0 | 0 | 13.8 |

TABLE 5-continued

Induced male sterility in pPCVTDEAC1 plants by flower treatment with N-acetyl-PPT and deacetylase activity in anthers

| Plant | Number of sterile or pollen-reduced flowers | | Deac. activity in anthers |
| --- | --- | --- | --- |
| | treated | untreated | [% L-PPT][1] |
| pPCT16 | 10 | 0 | 20.4 |

[1]based on the radioactivity employed ([$^{14}$C]—N-acetyl-L-PPT)

Example 6

Isolation and Identification of a Deacetylase having Specificity for N-acetylphosphinothricin from Comamonas Acidovorans A soil sample from Bangkok was suspended in mineral salt medium (0.5 g of $K_2HPO_4$, 0.2 g of $MgSO_4$, 2 g of $(NH_4)_2SO_4$, 0.01 g of $FeSO_4$ in 980 ml of $H_2O$), which contained chitin (2 g/l) as the only carbon source and subsequently incubated at 30° C. for 48 hours. Transfer to fresh mineral salt medium then took place and after incubation for a further 48 hours dilution series were plated out on LB medium (Miller, Experiments in molecular genetics, Cold Spring Harbour Laboratory Press).

Among the growing colonies, also found were those of a bacterial strain which distinguishes itself in pure culture by a very good utilization of N-acetyl glutamate as the only carbon source (streaking-out on mineral salt medium with N-acetyl glutamate (2 g/l, add as a sterile-filtered solution to autoclaved mineral salt medium with 14 g/l of agar) leads in the course of incubation at 30° C. for 12 hours to the formation of clearly visible colonies).

The deacetylation of N-acetyl-PPT was detected as described above. The strain provided with the laboratory description B6 was identified by the DSM as Comamonas acidovorans (DSM 11070).

Example 7

Cloning of the Deactylase Gene from Comamonas Acidovorans

Total DNA from Comamonas acidovorans was isolated, digested with EcoRI and ligated with likewise EcoRI-digested DNA of the vector pACYC184 (Cang and Cohen, 1978, J. Bacteriol. 134, 1141–1156). The ligation batch was used for the electroporation of the *E. coli* argE mutant XSID2 (Mountain et al., 1984, Mol. Gen. Genet. 197, 82–89). By selection for complementation of the arginine auxotrophy, it was possible to isolate an EcoRI fragment 8.9 kb in size from the genome of C. acidovorans, which is adequate for the complementation. By subcloning, the complementing region could be restricted to a fragment 1.4 kb in size. This is present in the derivative designated by pGK83 of the sequencing vector pSVB30 (Arnold and Puhler, 1988, Gene 70, 172–178).

Example 8

Sequencing of the Deacetylase Gene from Comamonas Acidovorans

The complementing fragment 1.4 kb (1387 base pairs) in size was completely sequenced as a double strand by known methods.

Example 9

Coding Region Analysis and Homology Comparison of the Sequenced Region

A coding region analysis showed an open reading frame from position 1 to 1206 (SEQ ID No. 3), which codes for a protein 402 amino acids in size (SEQ ID NO. 4).

The homology comparison with known genes from databanks shows a clear homology to an N-acyl-L-amidohydrolase from Bacillus stearothermophilus (ama, Sakanyan et al., 1993, Appl. Environ. Microbiol. 59, 3878–3888) and a hippurate hydrolase from Campylobacter jejuni (hitherto unpublished). In the protein comparison, the hippurate hydrolase has 43% of identical amino acids (Tab. 6). Moreover, at the DNA and protein level, the gene has a very conspicuous homology to the deacetylase gene isolated from Stenotrophomonas spec. Following the designation of the gene from Stenotrophomonas sp., the gene identified from C. acidovorans was designated by deac2.

TABLE 6

Homology comparison with known sequences

| Gene | Organism | Function | ident. AA | cons. AA |
|---|---|---|---|---|
| n.n | Campylobacter jejuni | Hippurate hydrolase (383 AS) | 43.1% | 60.0% |
| deac2 | Bacillus stearothermophilus | N-acyl-L-amido-hydrolase (370 AS) | 37.0% | 49.5% |

Example 10

Overexpression of the Deac2 Gene from Comamonas Acidovorans Plant Constructs To analyze the substrate specificity of the deac2 gene product from Comamonas acidovorans, this was overexpressed. To do this, the gene was cloned into a vector with a high copy number under control of the lacZ promoter. The expression efficiency, however, was restricted by the simultaneous translation, taking place in another reading frame, of the lacZ-alpha. This was therefore interrupted by introducing a stop codon, such that the vector pGK81 makes possible an overexpression of the deac2 gene which is not adversely effected by the lacZ gene. It was also possible to detect this phenotypically, since this construct has a markedly higher complementation of an E. coli argE mutant.

Figure 4:
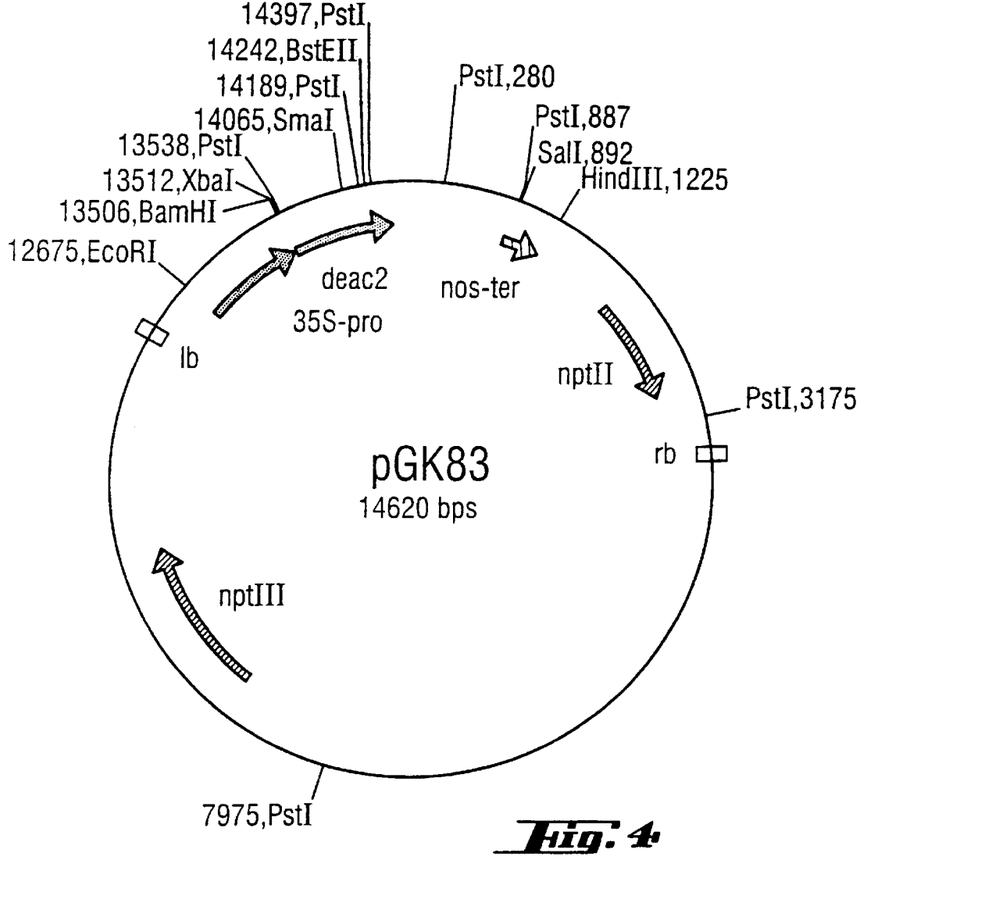
Figure 5:
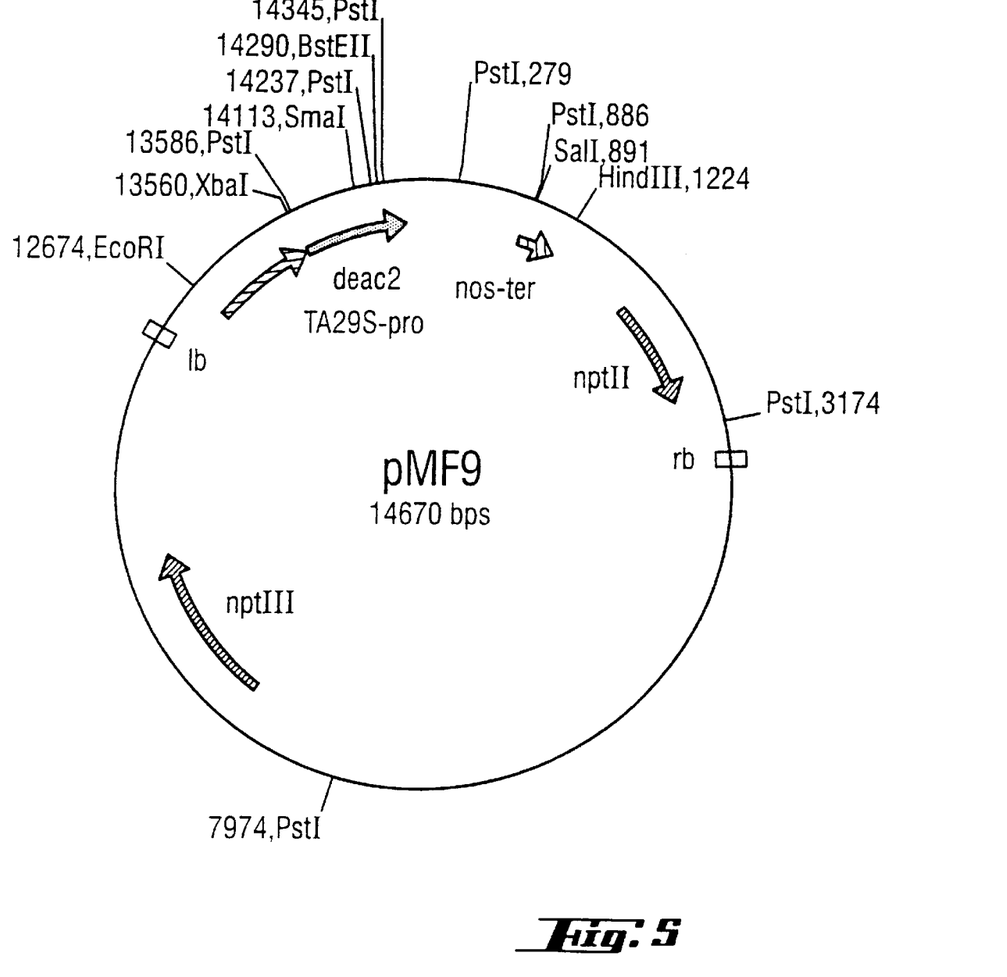
FIG. 5 Map of the plasmid pMF9

For the transformation of plants, the deac2 structural gene was recloned using the binary vector pROK1 (Baulcombe et al. 1986, Nature, 321: 446–449) after the constitutive 35S promoter or the tapetum-specific promoter TA-29. The expression plasmids pGK83 and pMF9 obtained are shown in the figures.

Example 11

Investigation of the Substrate Specificity of the Deac2 Gene Product from Comamonas Acidovorans To investigate the substrate specificity of the deac2 gene product from Comamonas acidovorans, cells of E. coli strain XLI blue permeabilized by toluene/ethanol treatment were used with and without the vector pGK81. The induction of the deac2 gene repressed by the $Lac^i$ repressor present in this strain could be achieved by IPTG treatment. The permeabilized cells were incubated for 3 hours at 30° C. with various N-acetylated amino acids (final concentration 25 mM) and the supernatants were investigated with the aid of an amino acid analyzer. It turned out here that more than 20% of the N-acetylornithine made available was converted. For N-acetyl-phosphinothricin too, an increasing deacetylation to phosphinothricin, analogous to the concentration of N-acetylphosphinothricin employed, could be found (Table 7).

TABLE 7

Conversion of N-acetylated amino acids by the deac2 gene product

| N-acetyl-ornithine | N-acetyl-phenylalanine | N-acetylphosphinothricin | | |
|---|---|---|---|---|
| (25 mM) | (25 mM) | (12.5 mM) | (25 mM) | (50 mM) |
| 5860 nM | <5 nM | 8.0 nM | 20.0 nM | 44.7 nM |

The concentrations of the N-acetylated amino acids employed and the amino acids formed by deacetylation are indicated.

What is claimed is:

1. An isolated DNA molecule encoding a protein having the biological activity of an N-acetylphosphinothricin deacetylase and having the anino acid sequence of SEQ ID No. 4.

2. The isolated DNA molecule of claim 1, which comprises the nucleotide sequence of SEQ ID No. 3 or a sequence which deviates from this sequence within the bounds of code degeneracy.

3. The isolated DNA molecule of claim 1, wherein the DNA molecule is isolated from Stenotrophornonas sp., deposited as DSM 9734.

4. The isolated DNA molecule of claim 1, wherein the DNA molecule is isolated from Comamnonas, deposited as DSM 11070.

5. A method of producing plants with inducibly destroyable parts, the method comprising:
   a) transforming plant cells with a deacetylase gene comprising the DNA sequence as claimed in claim 1 encoding a protein having the biological activity of a deacetylase under the control of a promoter directing expression in specific plant parts; and
   b) regenerating said plants from said plant cells, wherein said plants have parts which can be inducibly destroyed by treatment with N-acetylphosphino-thricin.

6. The method as claimed in claim 5, wherein inducibly male sterile or female sterile plants are obtained by the specific expression of said deacetylase gene.

7. A plant cell which comprises the isolated DNA molecule as claimed in claim 1.

8. A plant which comprises the isolated DNA molecule as claimed in claim 1.

9. An isolated DNA molecule encoding a protein, having the biological activity of an N-Acetyl-Phosphinothricin-Deacetylase, selected from the group consisting of:
   a) DNA molecules which can be isolated from Stenotrophomonas sp., deposited under DSM No. DSM 9734; and
   b) DNA molecules which can be isolated from *Comamonas acidovorans*, deposited under DSM No. DSM 11070.

10. A method of producing plants with inducibly destroyable parts, the method comprising:
   a) transforming plant cells with a deacetylase gene comprising the DNA molecule as claimed in claim 9, encoding a protein having the biological activity of a deacetylase, under the control of a promoter directing expression in specific plant parts; and
   b) regenerating said plants from said plant cells, wherein said plants have parts which can be inducibly destroyed by treatment with N-acetyl-PPT.

11. The method of claim 10, wherein inducibly male sterile or female sterile plants are obtained by the specific expression of said deacetylase gene.

12. A plant cell which comprises the isolated DNA molecule as claimed in claim 9.

13. A plant which comprises the isolated DNA molecule as claimed in claim 9.

* * * * *

UNITED STATES PATENT AND TRADEMARK OFFICE
CERTIFICATE OF CORRECTION

PATENT NO. : 6,177,616 B1
DATED : January 23, 2001
INVENTOR(S) : Bartsch et al.

It is certified that error appears in the above-identified patent and that said Letters Patent is hereby corrected as shown below:

Claim 1,
Line 3, change "anino" to -- amino --.

Claim 3,
Line 2, change "Stenotrophornonas" to -- Stenotrophomonas --.

Claim 4,
Line 2, change "Comamnonas" to -- Comamonas --.

Claim 5, (under b)
Last line, change "N-acetylphosphino-thricin" to -- N-acetyl-phosphinothricin --.

Signed and Sealed this

Fifth Day of March, 2002

*Attest:*

JAMES E. ROGAN
*Attesting Officer*   *Director of the United States Patent and Trademark Office*

SEQUENCE LISTING

<160> NUMBER OF SEQ ID NOS: 4

<210> SEQ ID NO 1
<211> LENGTH: 1365
<212> TYPE: DNA
<213> ORGANISM: Stenotrophomonas maltophilia

<400> SEQUENCE: 1
atgatccgca agaccgttct gttgactgcg ctgtcctgcg ccctggcctc cgcgacagcc    60

-continued

```
accgccgccg aaggccagcg gcccgaggtg gaggccgccg ccgcgcgcct gcagcggcag      120
gtggtggagt ggcgccgcga tttccaccag catccggagc tgtccaaccg cgaggtgcgc      180
accgccgcca aggtggccga gcgcctgcgc gcgatgggcc tgcaaccgca gaccggcgtc      240
gccgtgcacg gcgtggtggc gatcatcaag ggcgccctgc cggggccgaa gatcgccctg      300
cgcgcggaca tggacgcgct gccggtgacc gaacagaccg gctgccgtt cgcctccacc       360 gccacgccg agtaccgcgg cgagaaggtc ggggtgatgc atgcctgcgg ccacgacgcc       420
cataccgcca ccctgctcgg cgtggccgac gcgctggtgg ccatgcgcga cacgctgccc     480
ggcgaagtaa tgctgatctt ccagccggcc gaggaaggcg cgccgccgcc ggagcagggc     540
ggtgccgagc tgatgctcaa ggaggggctg ttcaaggagt tcaagccgga ggcggtgttc     600
ggcctgcacg tgttctccag cgtccaggcc gggcagatcg ccgtgcgcgg cggcccgctg     660
atggccgcct ccgaccgctt cgccatcacc gtcaacggcc gccagaccca tggctcggcg     720
ccctggaacg gcatcgatcc gattgtcgcc gcctccgacc tgatcggcac cgcgcagacc     780
atcgtcagcc gccgcgccaa cctgtccaag cagccggcgg tgctgacctt cggcgcgatc     840
aagggcggca tccgctacaa catcatcccc gactcggtgg agatggtcgg caccatccgc     900
accttcgacc cggacatgcg caagcagatc ttcgccgact gcgcaacgt cgccgagcac     960 accgctgccg catggcgcca ccgccaccac cgacatctac gagaaggacg gcaacccggc    1020
cacggtcaac gacccggcgc tgaccgcgcg catgctgccc agcctgcagg ccgtggtcgg    1080
caaggacaac gtctacgagc cgccgctgca gatgggctcg gaggacttct cgctgtatgc    1140
gcagcaggtg ccggcgatgt tcttcttcgt cggctccacc ggcgcgggca tcgacccggc    1200
caccgcgccc agcaaccact cgccgaagtt cctgctcgac gagaaggcgc tggacgtggg    1260
cctgcgcgcg ctgctgcagg tgtcgctgga ctatctgcac ggtggcaagg cggggtgacc    1320
cctgccagta tcgtgccccc gatacggaag aaggacctcc catga                    1365
```

<210> SEQ ID NO 2
<211> LENGTH: 454
<212> TYPE: PRT
<213> ORGANISM: Stenotrophomonas maltophilia

<400> SEQUENCE: 2

```
Met Ile Arg Lys Thr Val Leu Leu Thr Ala Leu Ser Cys Ala Leu Ala
  1               5                  10                  15

Ser Ala Thr Ala Thr Ala Ala Glu Gly Gln Arg Pro Glu Val Glu Ala
             20                  25                  30

Ala Ala Ala Arg Leu Gln Arg Gln Val Val Glu Trp Arg Arg Asp Phe
         35                  40                  45

His Gln His Pro Glu Leu Ser Asn Arg Glu Val Arg Thr Ala Ala Lys
     50                  55                  60

Val Ala Glu Arg Leu Arg Ala Met Gly Leu Gln Pro Gln Thr Gly Val
 65                  70                  75                  80

Ala Val His Gly Val Val Ala Ile Ile Lys Gly Ala Leu Pro Gly Pro
                 85                  90                  95

Lys Ile Ala Leu Arg Ala Asp Met Asp Ala Leu Pro Val Thr Glu Gln
            100                 105                 110

Thr Gly Leu Pro Phe Ala Ser Thr Ala Thr Ala Glu Tyr Arg Gly Glu
        115                 120                 125

Lys Val Gly Val Met His Ala Cys Gly His Asp Ala His Thr Ala Thr
    130                 135                 140
```

```
Leu Leu Gly Val Ala Asp Ala Leu Val Ala Met Arg Asp Thr Leu Pro
145                 150                 155                 160

Gly Glu Val Met Leu Ile Phe Gln Pro Ala Glu Glu Gly Ala Pro Pro
                165                 170                 175

Pro Glu Gln Gly Gly Ala Glu Leu Met Leu Lys Glu Gly Leu Phe Lys
                180                 185                 190

Glu Phe Lys Pro Glu Ala Val Phe Gly Leu His Val Phe Ser Ser Val
            195                 200                 205

Gln Ala Gly Gln Ile Ala Val Arg Gly Pro Leu Met Ala Ala Ser
    210                 215                 220

Asp Arg Phe Ala Ile Thr Val Asn Gly Arg Gln Thr His Gly Ser Ala
225                 230                 235                 240

Pro Trp Asn Gly Ile Asp Pro Ile Val Ala Ala Ser Asp Leu Ile Gly
                245                 250                 255

Thr Ala Gln Thr Ile Val Ser Arg Arg Ala Asn Leu Ser Lys Gln Pro
            260                 265                 270

Ala Val Leu Thr Phe Gly Ala Ile Lys Gly Gly Ile Arg Tyr Asn Ile
            275                 280                 285

Ile Pro Asp Ser Val Glu Met Val Gly Thr Ile Arg Thr Phe Asp Pro
290                 295                 300

Asp Met Arg Lys Gln Ile Phe Ala Asp Leu Arg Asn Val Ala Glu His
305                 310                 315                 320

Thr Ala Ala Ala Trp Arg His Arg His Arg His Leu Arg Glu Gly
                325                 330                 335

Arg Gln Pro Gly His Gly Gln Arg Pro Gly Ala Asp Arg Ala His Ala
                340                 345                 350

Ala Gln Pro Ala Gly Arg Gly Arg Gln Gly Gln Arg Leu Arg Ala Ala
            355                 360                 365

Ala Ala Asp Gly Leu Gly Gly Leu Leu Ala Val Cys Ala Ala Gly Ala
            370                 375                 380

Gly Asp Val Leu Leu Arg Arg Leu His Arg Arg Gly His Arg Pro Gly
385                 390                 395                 400

His Arg Ala Gln Gln Pro Leu Ala Glu Val Pro Ala Arg Arg Glu Gly
                405                 410                 415

Ala Gly Arg Gly Pro Ala Arg Ala Ala Gly Val Ala Gly Leu Ser
            420                 425                 430

Ala Arg Trp Gln Gly Gly Val Thr Pro Ala Ser Ile Val Pro Pro Ile
            435                 440                 445

Arg Lys Lys Asp Leu Pro
    450

<210> SEQ ID NO 3
<211> LENGTH: 1273
<212> TYPE: DNA
<213> ORGANISM: Stenotrophomonas maltophilia

<400> SEQUENCE: 3
atggccttgc tgcaggagct gctggacagc gcacccgaga tcaccgcgct gcgccgcgac      60
atacatgccc atcccgaact gtgcttcgag gaactgcgca ccgccgacct ggtggcccgg     120
cagctcgaag gctggggcat tgccgtgcac cgcggcctgg gccgcacggg cgtggtgggc     180
accatccacg gcgtgacgg cggcgccagc ggccgggcca tcgggctgcg cgccgacatg     240
gacgccctgc ccatgcagga gttcaacacc ttcgagcacg ccagccgcca cgccggaaaa     300
```

-continued

```
atgcatgcct gcggacatga cggccatgtc gccatgctgc tggccgccgc gcagtacctg    360
gccgtgcacc gcgacagctt cgagggcacg gtgcacctga tcttccagcc ggccgaagag    420
ggcggcggcg ggcgcgcga gatggtcgag acggcctgt tcacccagtt ccccatgcag     480
gccgtgttcg gcatgcacaa ctggccgggc atgaaggccg gcaccatgcc gtgggccccg    540
ggcccggcca tggcgtcgag caacgagttc cgcatcgtcg tgcgcggcaa gggcggccac    600
gcggccatgc cgcacatggt gatcgacccg ctgcccgtgg cggcccagct catcctgggc    660
ctgcagacca tcgtcagccg caacgtcaag cccatcgagg cgggcgtggt ctcggtcacc    720
atggtccatg cgggcgaggc cacgaacgtg gtgcccgaca gcgtggagct gcagggcacg    780
gtgcgcacct tcacgctgga ggtgctggac ctgatcgagc ggcgcatgaa ggccctggcc    840
gagagcatct gcgcggcgca tgacacgcgc tgcgagttcg agttcgtgcg caactacccg    900
cccaccatca actccgcccc ggaggccgag ttcgcacgcc gcgtcatggc cgaggtcgtg    960
ggcgaggcca acgtgctgcc ccaggagccg tccatgggcg ccgaggactt cgccttcatg   1020
ctgctggaaa agcccggcgc ctactgcttc atcgccaatg gcgacggcga ccaccgcgcc   1080
atcggccacg gcggcggtcc ctgcacgctg cacaaccca gctacgactt caacgaccag   1140
ctgattccgc agggcgccac gttctgggtg aagctggccc agcgctggct gagcgagccc   1200
acgcgctgag gccttgcggg gtccggccga caccggcatg tcacacaccg cacctagcat   1260
gcggtccctg tga                                                      1273
```

<210> SEQ ID NO 4
<211> LENGTH: 402
<212> TYPE: PRT
<213> ORGANISM: Stenotrophomonas maltophilia

<400> SEQUENCE: 4

```
Met Ala Leu Leu Gln Glu Leu Leu Asp Ser Ala Pro Glu Ile Thr Ala
 1               5                  10                  15

Leu Arg Arg Asp Ile His Ala His Pro Glu Leu Cys Phe Glu Glu Leu
            20                  25                  30

Arg Thr Ala Asp Leu Val Ala Arg Gln Leu Glu Gly Trp Gly Ile Ala
        35                  40                  45

Val His Arg Gly Leu Gly Arg Thr Gly Val Val Gly Thr Ile His Gly
    50                  55                  60

Arg Asp Gly Gly Ala Ser Gly Arg Ala Ile Gly Leu Arg Ala Asp Met
65                  70                  75                  80

Asp Ala Leu Pro Met Gln Glu Phe Asn Thr Phe Glu His Ala Ser Arg
                85                  90                  95

His Ala Gly Lys Met His Ala Cys Gly His Asp Gly His Val Ala Met
            100                 105                 110

Leu Leu Ala Ala Ala Gln Tyr Leu Ala Val His Arg Asp Ser Phe Glu
        115                 120                 125

Gly Thr Val His Leu Ile Phe Gln Pro Ala Glu Glu Gly Gly Gly Gly
    130                 135                 140

Ala Arg Glu Met Val Glu Asp Gly Leu Phe Thr Gln Phe Pro Met Gln
145                 150                 155                 160

Ala Val Phe Gly Met His Asn Trp Pro Gly Met Lys Ala Gly Thr Met
                165                 170                 175

Pro Trp Ala Pro Gly Pro Ala Met Ala Ser Ser Asn Glu Phe Arg Ile
            180                 185                 190

Val Val Arg Gly Lys Gly Gly His Ala Ala Met Pro His Met Val Ile
```

-continued

```
                    195                 200                 205
Asp Pro Leu Pro Val Ala Ala Gln Leu Ile Leu Gly Leu Gln Thr Ile
    210                 215                 220

Val Ser Arg Asn Val Lys Pro Ile Glu Ala Gly Val Val Ser Val Thr
225                 230                 235                 240

Met Val His Ala Gly Glu Ala Thr Asn Val Val Pro Asp Ser Val Glu
                245                 250                 255

Leu Gln Gly Thr Val Arg Thr Phe Thr Leu Glu Val Leu Asp Leu Ile
                260                 265                 270

Glu Arg Arg Met Lys Ala Leu Ala Glu Ser Ile Cys Ala Ala His Asp
                275                 280                 285

Thr Arg Cys Glu Phe Glu Phe Val Arg Asn Tyr Pro Pro Thr Ile Asn
    290                 295                 300

Ser Ala Pro Glu Ala Glu Phe Ala Arg Arg Val Met Ala Glu Val Val
305                 310                 315                 320

Gly Glu Ala Asn Val Leu Pro Gln Glu Pro Ser Met Gly Ala Glu Asp
                325                 330                 335

Phe Ala Phe Met Leu Leu Glu Lys Pro Gly Ala Tyr Cys Phe Ile Ala
                340                 345                 350

Asn Gly Asp Gly Asp His Arg Ala Ile Gly His Gly Gly Gly Pro Cys
                355                 360                 365

Thr Leu His Asn Pro Ser Tyr Asp Phe Asn Asp Gln Leu Ile Pro Gln
    370                 375                 380

Gly Ala Thr Phe Trp Val Lys Leu Ala Gln Arg Trp Leu Ser Glu Pro
385                 390                 395                 400

Thr Arg
```